(12) United States Patent
Kokubun

(10) Patent No.: US 8,442,292 B2
(45) Date of Patent: May 14, 2013

(54) X-RAY CT APPARATUS

(75) Inventor: Hiroto Kokubun, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 160 days.

(21) Appl. No.: 12/999,175

(22) PCT Filed: Jun. 29, 2009

(86) PCT No.: PCT/JP2009/061818
§ 371 (c)(1),
(2), (4) Date: Dec. 15, 2010

(87) PCT Pub. No.: WO2010/001840
PCT Pub. Date: Jan. 7, 2010

(65) Prior Publication Data
US 2011/0164800 A1    Jul. 7, 2011

(30) Foreign Application Priority Data

Jul. 1, 2008  (JP) ................................. 2008-172067

(51) Int. Cl.
*G06K 9/00*    (2006.01)
(52) U.S. Cl.
USPC ........... 382/131; 382/132; 382/128; 382/207; 378/8; 378/5; 378/15; 378/62; 378/4
(58) Field of Classification Search .................. 382/131, 382/132, 128; 378/19, 15, 8, 4, 62; 600/425, 600/428
See application file for complete search history.

(56) References Cited

U.S. PATENT DOCUMENTS

| 4,020,343 | A | * | 4/1977 | Shimaya et al. ............. 250/310 |
| 4,812,996 | A | * | 3/1989 | Stubbs .......................... 702/123 |
| 5,155,836 | A | * | 10/1992 | Jordan et al. .................... 703/23 |
| 7,209,779 | B2 | * | 4/2007 | Kaufman et al. ............. 600/425 |
| 2001/0001137 | A1 | * | 5/2001 | Alexander ....................... 702/68 |

(Continued)

FOREIGN PATENT DOCUMENTS

| CN | 1615104 A | 5/2005 |
| CN | 1933781 A | 3/2007 |

(Continued)

OTHER PUBLICATIONS

International Search Report in PCT/JP2009/061818.
Chinese official action (English translation enclosed herewith) dated Sep. 5, 2012 in connection with corresponding Chinese patent application No. 200980123670.X.

*Primary Examiner* — Stephen R Koziol
*Assistant Examiner* — Shaghayegh Azima
(74) *Attorney, Agent, or Firm* — Cooper & Dunham LLP

(57) ABSTRACT

An X-ray CT apparatus that can efficiently set a scanning condition in a scanning operation of a periodically moving internal organ such as a heart or the like is provided. The X-ray CT apparatus collects electrocardiographic information by using a periodic motion measuring device 6 (S1). Subsequently, an operator input a time resolution rate corresponding to time resolution expected in a target examination (S2). Subsequently, the X-ray CT apparatus calculates a scanning condition under which the input time resolution rate can be implemented (S3). Subsequently, the X-ray CT apparatus images a heart under the scanning condition calculated in S3 (S4). Subsequently, the X-ray CT apparatus reconstructs an electrocardiographic-synchronous image by using the scanning data obtained in S4 and the electrocardiographic information (S5). Subsequently, the X-ray CT apparatus displays the electrocardiographic-synchronous image reconstructed in S5 on a display device 5 (S6).

8 Claims, 9 Drawing Sheets

U.S. PATENT DOCUMENTS

| | | | |
|---|---|---|---|
| 2004/0136490 A1* | 7/2004 | Edic et al. | 378/4 |
| 2004/0179644 A1* | 9/2004 | Tsuyuki | 378/8 |
| 2004/0254447 A1* | 12/2004 | Block et al. | 600/410 |
| 2005/0069081 A1* | 3/2005 | Kokubun et al. | 378/15 |
| 2005/0129176 A1* | 6/2005 | Kokubun et al. | 378/95 |
| 2005/0209888 A1 | 9/2005 | Oowaki et al. | |
| 2006/0140337 A1* | 6/2006 | Miyazaki et al. | 378/8 |
| 2006/0291615 A1* | 12/2006 | Nishide et al. | 378/8 |
| 2007/0183557 A1 | 8/2007 | Manzke et al. | |
| 2007/0189436 A1* | 8/2007 | Goto et al. | 378/4 |
| 2008/0056547 A1* | 3/2008 | Kokubun et al. | 382/128 |

FOREIGN PATENT DOCUMENTS

| | | |
|---|---|---|
| JP | 2004-275440 | 10/2004 |
| JP | 2005-168948 | 6/2005 |
| JP | 2006-150033 | 6/2006 |
| JP | 2007-408 | 1/2007 |
| WO | WO2006/018763 A1 | 2/2006 |

* cited by examiner

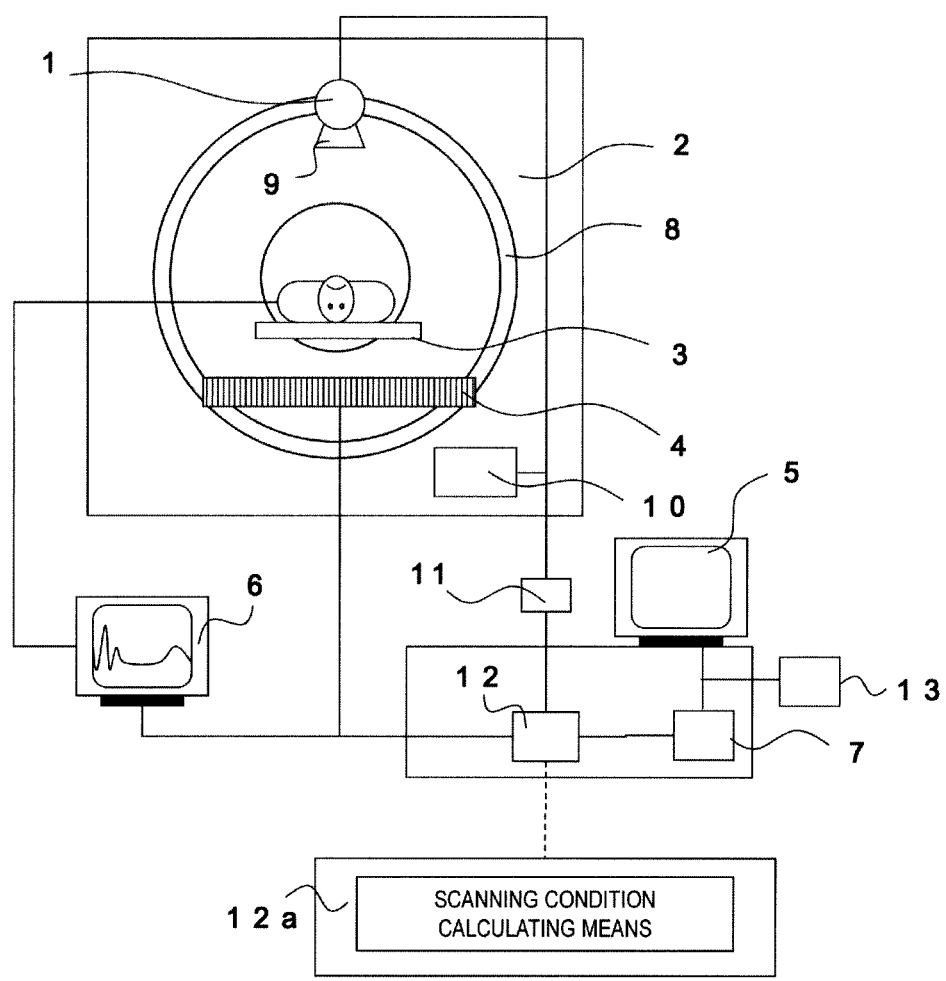
F I G. 1

F I G. 3
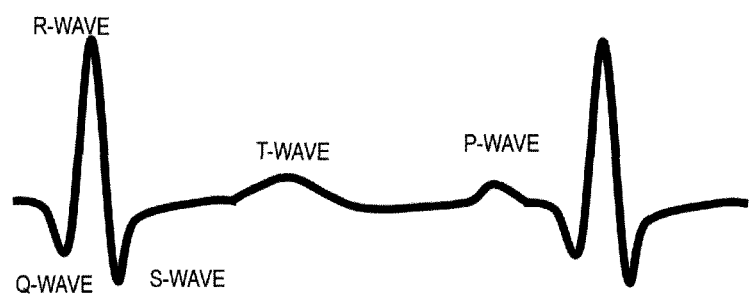
F I G. 4
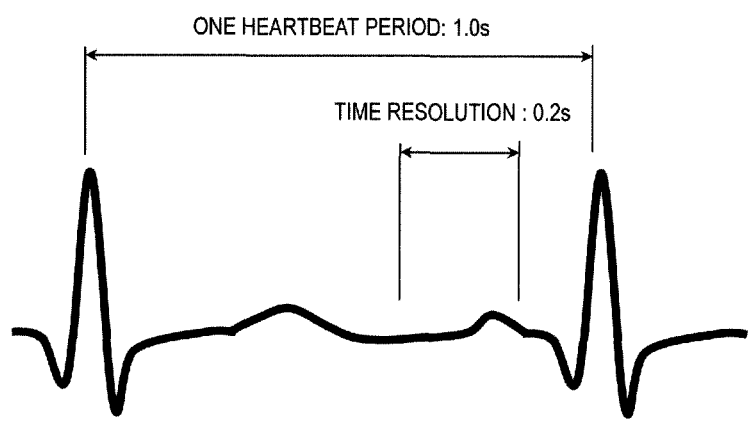

F I G. 7
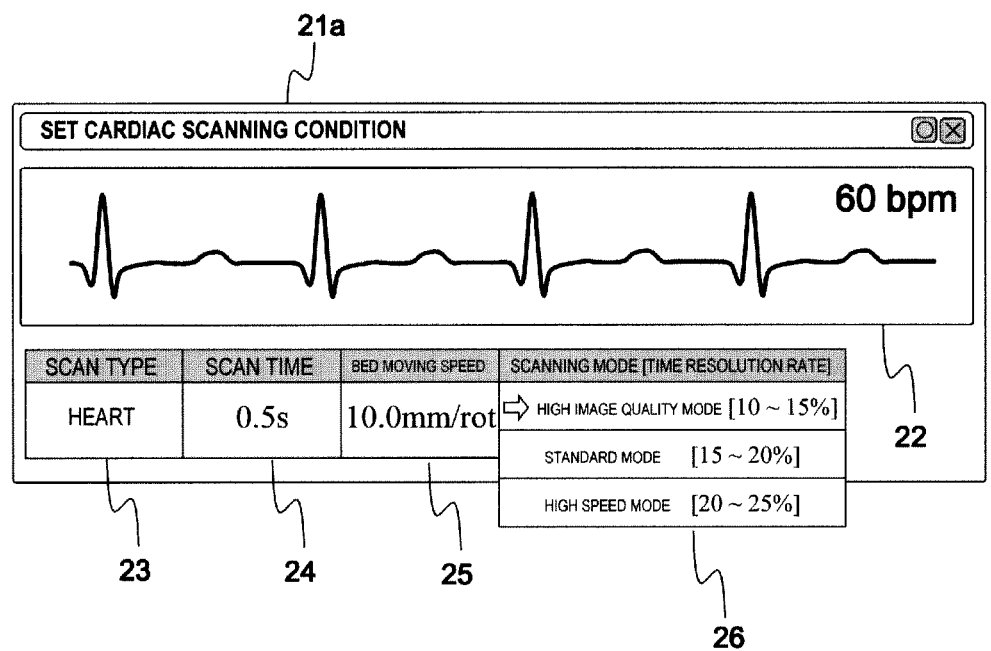

F I G. 8
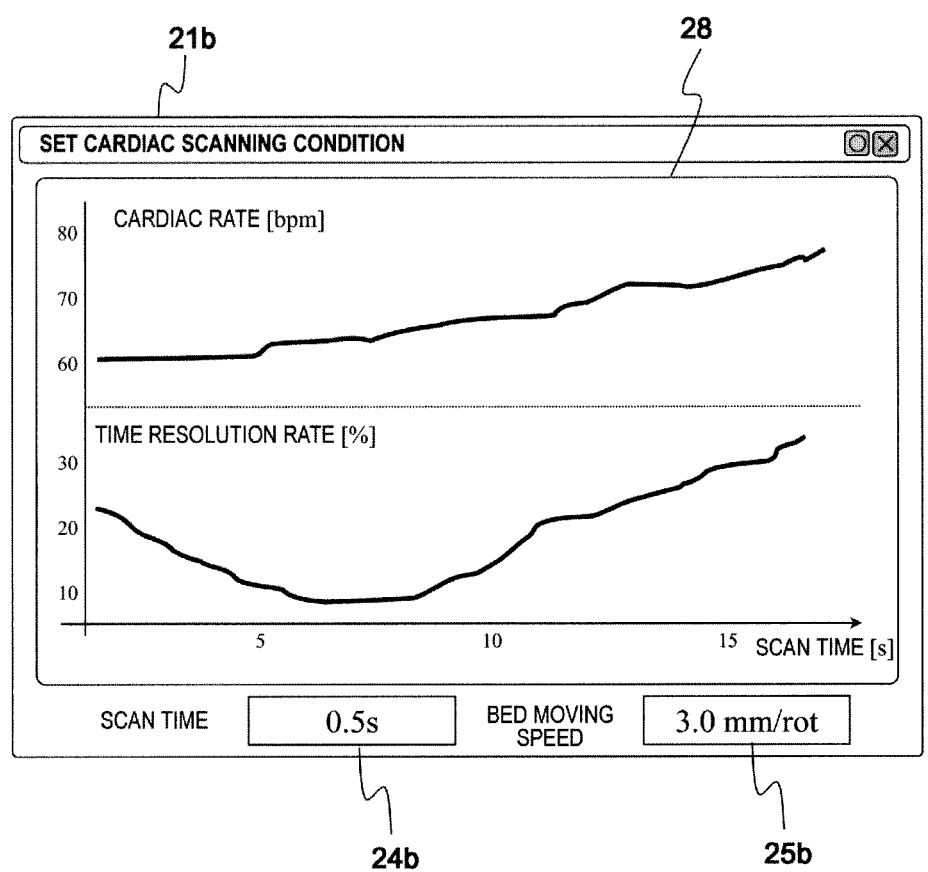

F I G. 1 0
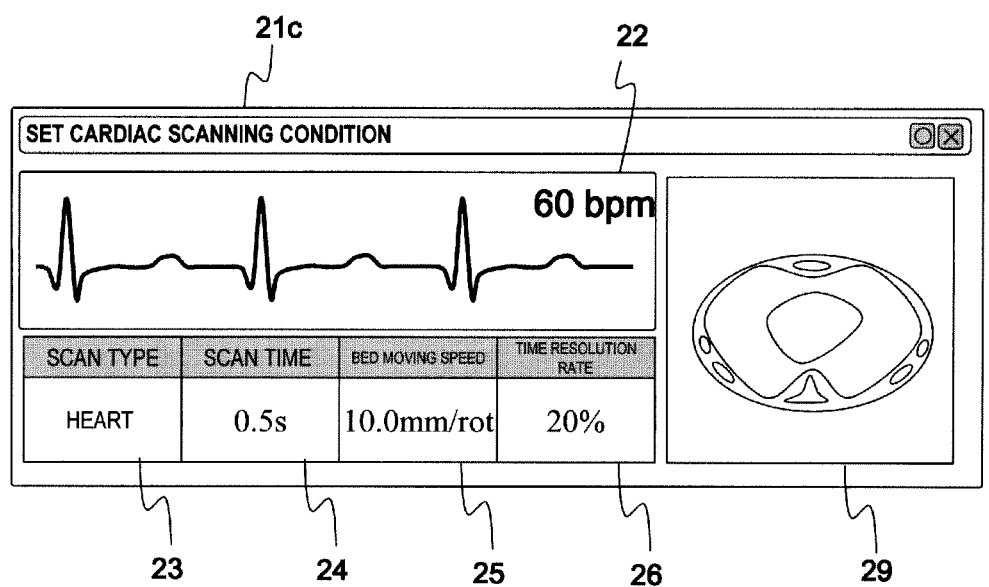

X-RAY CT APPARATUS

TECHNICAL FIELD

The present invention relates to an X-ray CT (Computed Tomography) apparatus, and particularly to an X-ray CT apparatus aiming at cardiovascular scanning.

BACKGROUND ART

When a moving body site is imaged by an X-ray CT apparatus, an artifact caused by movement occurs in an obtained tomogram. In order to reduce this artifact, a biomedical sensor such as an electrocardiograph, a respiration sensor or the like is generally used and also a measurement based on equipment for converting a physiological periodic motion to an electrical signal is executed in combination. Scanning and image reconstruction are executed by using the thus-obtained electrical signal. Particularly, a reconstructing method targeting a heart is called as an electrocardiographic-synchronous reconstructing method. According to this method, an electrical signal measured by an electrocardiograph is added to scanning data and collected, and image reconstruction is executed on the basis of obtained electrocardiographic information, whereby a cardiac tomography at any cardiac time phase can be obtained.

For example, according to a mechanism of Patent Document 1, scanning data which are different in scan or view at the same cardiac time phase (hereinafter referred to as "divisional scanning data") are collected from plural heartbeats by using R-wave of an electrocardiographic waveform as a benchmark. The thus-collected scanning data are combined with one another to reconstruct an image, whereby time resolution can be enhanced.

However, in the divisional type reconstruction based on the mechanism of the Patent Document 1 or the like, the collection pattern of the divisional scanning data varies in accordance with a cardiac rate and a scanning condition, and thus the time resolution varies. The time resolution varies depending on the cardiac rate, the scan speed and the bed moving speed. For example, as the bed moving speed is smaller, the number of collectable divisional scanning data is larger and thus the time resolution is higher. As described above, the time resolution of the divisional type reconstruction is affected by the cardiac rate of a patient and the scanning condition. In an actual scanning operation, a scanning condition is required to be determined in consideration of a breadth-holding time and an exposed dose so as to obtain image quality necessary to make a diagnosis.

For example, there is known a method of determining a scanning condition by using the number of divisional scanning data to be collected as an index to create one image (hereinafter referred to as "first method"). According to the first method, an optimum scanning condition is selected to collect divisional scanning data whose number is specified by an operator. In general, as the number of divisional scanning data to be collected is increased, higher time resolution can be obtained. However, it is necessary to reduce the bed moving speed, so that the exposed dose increases. Conversely, as the number of divisional scanning data is reduced, the bed moving speed can be set to a higher value, so that the exposed dose is reduced, however, the time resolution is lowered.

Furthermore, there is also known a method of determining a scanning condition by using the bed moving speed as an index (hereinafter referred to as "second method"), for example. According to the second method, scanning is executed at a bed moving speed specified by an operator, and image reconstruction is performed by using collectable divisional scanning data. In general, as the bed moving speed is lower, a larger amount of divisional projection data can be collected and thus the time resolution is higher. Conversely, as the bed moving speed is higher, collectable divisional projection data is less and thus the time resolution is lowered.

PRIOR ART DOCUMENT

Patent Document

Patent Document 1: JP-A-2000-107174

SUMMARY OF THE INVENTION

Problem to be Solved by the Invention

However, in the first method or the second method described above, the scanning condition such as the number of divisional scanning data, the bed moving speed or the like must be adjusted in accordance with the cardiac rate of a patient. When the cardiac rate of the patient is high, that is, when the beat period of a heart is short, the time for which the heart is stopped is short. Therefore, in order to create a tomogram necessary for a diagnosis, it is necessary to enhance the time resolution by adjusting parameters. Conversely, when the cardiac rate of a patient is low, that is, when the beat period of a heart is long, the time for which the heart is stopped is long. Therefore, it is required to lower the time resolution by adjusting parameters, thereby optimizing the exposed dose. The cardiac rate is affected and varied by a scanning condition such as the health condition of a patient, a breath-holding time or the like, and thus the operator must carefully adjust the scanning parameters in accordance with the cardiac rate. This work imposes large labor on the operator, thereby making a scanning operation cumbersome and causing deterioration of the examination efficiency.

Furthermore, in the first method and the second method described above, it is difficult for the operator to grasp the effect of the scanning parameters such as the number of divisional scanning data, the bed moving speed, etc. on a finally obtained tomogram. In order to determine the scanning parameters, the operator must first grasp the time resolution when any parameters are set. In order to perform this work, the operator is required to sufficiently learn the cardiac scanning method and also understand the scanning function inherent in the apparatus. Furthermore, whether the obtained time resolution satisfies an examination purpose must be carefully considered in consideration of the cardiac rate of the patient. In order to perform this work, the operator is required to be skilled in the scanning technique. Even when the operator is skilled in the scanning technique, a load is large, so that the scanning work is made cumbersome and the examination efficiency is deteriorated.

The present invention has been implemented in view of the problem faced by the divisional type reconstruction described above, and has an object to provide an X-ray CT apparatus in which a scanning condition can be efficiently set in a scanning operation of a periodically moving internal organ such as a heart or the like.

Means of Solving the Problem

In order to attain the above object, according to a first invention, an X-ray CT apparatus which includes: an X-ray source for applying X-ray; an X-ray detector that is disposed so as to face the X-ray source while an examinee is sandwiched between the X-ray source and the X-ray detector and detects an X-ray dose transmitted through the examinee; a gantry that has the X-ray source and the X-ray detector mounted therein and is rotatable around the examinee; a bed that is movable while the examinee is put on the bed; a control device that controls the X-ray source, the X-ray detector, the gantry and the bed; a periodic motion measuring device that measures a periodic motion of the examinee; an image processing device that generates a reconstructed image of the examinee at any phase of the periodic motion on the basis of data of the X-ray dose and data of the periodic motion; and a display device that displays the reconstructed image, is characterized by including scanning condition calculating means that calculates a period of the periodic motion from the data of the periodic motion and calculates a scanning condition by using as an index a time resolution rate corresponding to the ratio between a time resolution of the reconstructed image and the period.

The first invention may be further provided with means through which the operator inputs the time resolution rate, and the scanning condition calculating means may calculate a scanning condition on the basis of the data of the periodic motion so as to satisfy the time resolution rate input by the operator. By setting the time resolution rate as an input value as described above, the operator can set the scanning condition by using as an index the time resolution rate which directly represents goodness of image quality.

Furthermore, the first invention may be further provided with means that divides a range of the time resolution rate into plural parts and displays a scanning mode of each divided range of the time resolution rate on the display device, and the scanning condition calculating means may calculate a scanning condition on the basis of the data of the periodic motion so as to fall into the range of the time resolution rate corresponding to the scanning mode selected by the operator. Accordingly, even when a feasible scanning condition is limited, the scanning condition can be efficiently set.

Still furthermore, the first invention may be further provided with means that calculates variation of the time resolution rate on the basis of the data of the periodic motion of a fixed period measured by the periodic motion measuring device and displays the calculated variation of the time resolution rate on the display device. Accordingly, variation of a time resolution rate which is predicted when scanning is executed under a desired scanning condition can be visually checked, and the operator can determine the scanning condition efficiently.

Still furthermore, the first invention may be further provided with means that displays a rectangle for specifying and inputting the time resolution rate on the display device while superimposing the rectangle on a waveform representing the data of the periodic motion measured by the periodic motion measuring device. By adjusting the position and width of the rectangle on the waveform, a tomogram having little motional artifact can be obtained with high precision and further without being dependent on individual difference of the examinee.

Still furthermore, in the first invention, the periodic motion may be cardiac pulsation of the examinee, and the scanning condition calculating means may calculate the scanning condition with respect to the time from T-wave till R-wave in one period. By setting the time from the T-wave till the R-wave as a reference time, it is possible to set the scanning condition interlockingly with the cardiac rate, and thus the scanning condition can be set with higher precision.

Still furthermore, the first invention may be further provided with means that displays a sample image corresponding to the time resolution rate on the display device. Accordingly, the operator can set the scanning condition efficiently.

Effect of the Invention

According to the present invention, there can be provided an X-ray CT apparatus that can efficiently set a scanning condition in a scanning operation of a periodically moving internal organ such as a heart or the like.

BRIEF DESCRIPTION OF THE DRAWINGS

FIG. 1 is a diagram showing the hardware construction of an X-ray CT apparatus.

FIG. 3 is a diagram showing an example of an electrocardiographic waveform.

FIG. 4 is a diagram showing one heartbeat period and expected time resolution of an examinee.

FIG. 7 is a diagram showing an example of a cardiac scanning condition setting screen 21a for inputting a time resolution rate as a scanning mode.

FIG. 8 is a diagram showing an example of a cardiac scanning condition setting screen 21b for representing a variation graph of the time resolution rate of a fixed period.

FIG. 10 is a diagram showing an example of a cardiac scanning condition setting screen 21c.

BEST MODE FOR CARRYING OUT THE INVENTION

Figure 2:
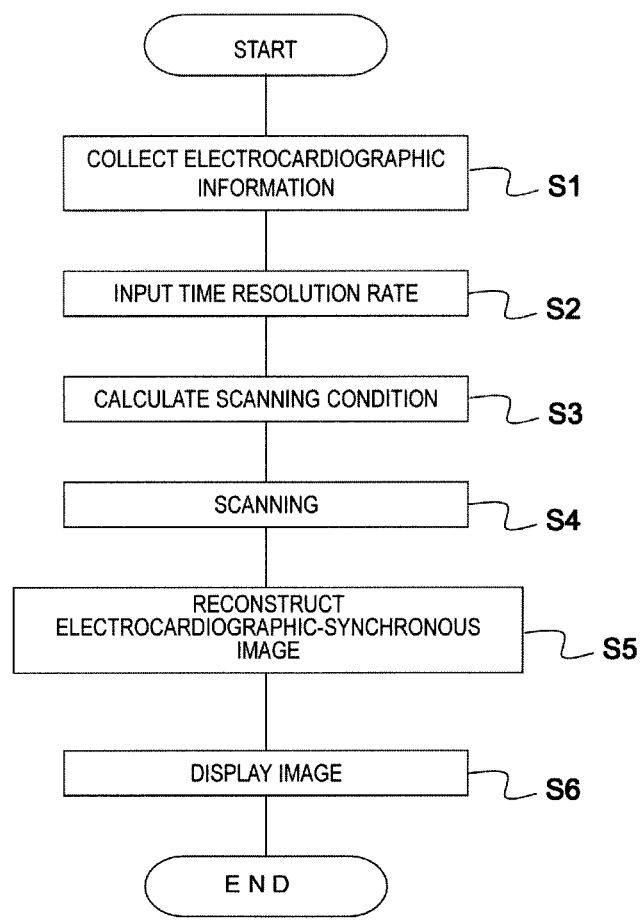
FIG. 2 is a flowchart showing reconstruction processing of a cardiac image.

An embodiment of the present invention will be described in detail with reference to the drawings.

(1. Construction of X-Ray CT Apparatus)

FIG. 1 is a diagram showing the hardware construction of an X-ray CT apparatus. The X-ray CT apparatus includes a scanner gantry 2, a bed 3, a display device 5, a periodic motion measuring device 6, an image processing device 7, a computer 12, an input device 13, etc.

The scanner gantry 2 has an X-ray tube 1, an X-ray detector 4, a rotational disc 8, a collimator 9, a rotational driving device 10, a measurement control device 11, etc. The X-ray tube 1 is an X-ray source and irradiates an examinee with X-ray. The X-ray detector 4 detects X-ray which is emitted from the X-ray tube 1 and transmitted through the examinee. The rotational disc 8 is rotated by the rotational driving device 10. The measurement control device 11 controls the rotational driving device 10, controls the intensity of X-ray generated from the X-ray tube 1 and detects measured data. The measurement control device 11 receives a control command from the computer 12. An operator inputs various kinds of data into the computer 12 through the input device 13.

The periodic motion measuring device 6 measures the periodic motion of the examinee. In the following description, a scanning target is assumed as a heart and the periodic motion measuring device 6 is assumed as an electrocardiograph, however, the image target and the periodic motion measuring device 6 are not limited to them. For example, when the scanning target is a lung, the periodic motion measuring device 6 may be a respirometer or the like. The image processing device 7 creates scanning data from measured data detected by the scanner gantry 2, and processes the scanning data into a CT image signal. The display device 5 displays setting screens for a CT image and a scanning condition, etc.

(2. Processing Content of X-Ray CT Apparatus)

FIG. 2 is a flowchart showing the reconstruction processing of a cardiac image. As shown in FIG. 2, the X-ray CT apparatus collects cardiac information by using the periodic motion measuring device 6 (S1).

FIG. 3 is a diagram showing an example of an electrocardiographic waveform. When a heartbeat period is calculated, the position of R-wave which is easy to specify the peak position thereof is normally used as a reference signal. However, the positions of P-wave, Q-wave, S-wave, T-wave may be used as a reference signal.

Subsequently, the operator inputs a time resolution rate expected in a target examination (S2). Specifically, the operator inputs the time resolution rate into the computer 12 through the input device 13. The time resolution rate is defined as the ratio between the time resolution of an image created by the image processing device 7 and a heartbeat period calculated on the basis of the data of the periodic motion measured by the periodic motion measuring device 6. In this embodiment of the present invention, not the time resolution, but the time resolution rate is treated as an input value. For example, with respect to (1) an image of 0.8 s in one heartbeat period and 0.2 s in time resolution and (2) an image of 1.0 s in one heartbeat period and 0.2 s in time resolution, the image of (1) is lower in image quality. On the other hand, with respect to (1) an image of 0.8 s in heartbeat period and 20% in time resolution rate and (2) an image of 1.0 s in heartbeat period and 20% in time resolution rate, both the images have the same level in image quality. Accordingly, as in the case of this embodiment of the present invention, by setting the time resolution rate as an input value, the operator can set a scanning condition by setting, as an index, the time resolution rate which directly represents the goodness of the image quality.

FIG. 4 is a diagram showing one heartbeat period of the examinee and the expected time resolution. As shown in FIG. 4, the one heartbeat period of the examinee is equal to 1.0 s. Furthermore, the time resolution expected in the target examination is equal to 0.2 s. In this case, the operator may input 0.2/1.0=0.2(20%) as the time resolution rate into the computer 12.

Figure 5:
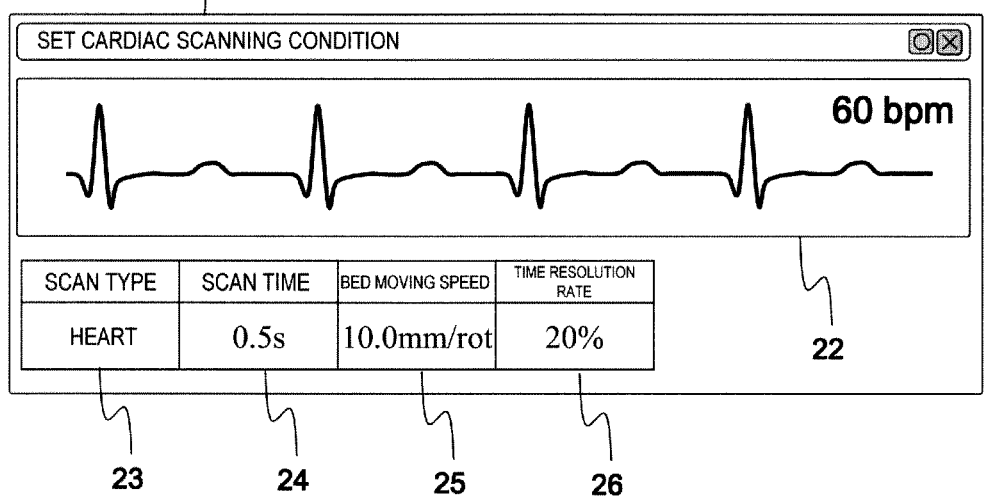
FIG. 5 is a diagram showing an example of a cardiac scanning condition setting screen 21.

FIG. 5 is a diagram showing an example of a cardiac scanning condition setting screen 21. The cardiac scanning condition setting screen 21 has screen items such as an electrocardiogram display portion 22, a scan type display portion 23, a scan time display portion 24, a bed moving speed display portion 25, a time resolution rate input portion 26, etc. Electrocardiographic information collected in S1 is displayed on the electrocardiogram display portion 22, and the electrocardiographic information is updated every fixed time. The scan type display portion 23, the scan time display portion 24 and the bed moving speed display portion 25 are boxes for representing calculation results of the computer 12, etc. The time resolution rate input portion 26 is a box for inputting. The time resolution rate input portion 26 may be set as a text box or a choice type such as a pull-down menu or the like.

Set values shown in FIG. 5 are set values corresponding to the one heartbeat period of the examinee and the expected time resolution shown in FIG. 4. The waveform of the cardiac rate of "60 bpm" is displayed in the electrocardiogram display portion 22. That is, the one heartbeat period of the examinee is equal to 1.0 s. As described above with reference to FIG. 4, "20%" is input in the time resolution rate input portion 26. "heart" is displayed in the scan type display portion 23, "0.5 s" is displayed in the scan time display portion 24, and "10.0 mm/rot" is displayed in the bed moving speed display portion 25.

Subsequently, the X-ray CT apparatus calculates a scanning condition under which the time resolution rate input in S2 can be implemented (S3). Specifically, a scanning condition calculating means 12a of the computer 12 first calculates time resolution necessary to obtain a target time resolution rate during the one heartbeat period measured in S1. This time resolution is calculated on the basis of one heartbeat period× time resolution rate. For example, when the one heartbeat period of the examinee is equal to 1.0 s, the time resolution to obtain the time resolution rate of 0.2 (20%) is calculated as 1.0×0.2=0.2 s. Here, an average value of plural heartbeats may be used as the one heartbeat period used for this calculation. The cardiac rate generally varies depending on various factors, and thus the calculation precision of the time resolution is expected to be enhanced by using the average value of plural heartbeats. Subsequently, the scanning condition calculating means 12a calculates a scanning condition necessary to implement the calculated time resolution. A scan speed and a bed moving speed are provided as representative parameters for adjusting the time resolution. The calculated scanning condition is displayed on the display device 5 as shown in FIG. 5.

The relationship between the time resolution and the scanning condition is determined depending on the specification of the X-ray CT apparatus, the scanning method, the electrocardiographic-synchronous reconstructing method, etc. Therefore, for example, a scanning condition table in which the time resolution rate and the scanning condition are associated with each other in accordance with the specification of the X-ray CT apparatus, the scanning method, the electrocardiographic-synchronous reconstructing method, etc. may be created in advance and stored in the measuring control device 11 or the computer 12. The scanning condition calculating means 12a may obtain the scanning condition corresponding to the time resolution rate input in S2 from the scanning condition table.

Subsequently, the X-ray CT apparatus images a heart under the scanning condition calculated in S3 (S4). At this time, the X-ray CT apparatus obtains scanning data and also obtains electrocardiographic information based on the periodic motion measuring device 6.

Subsequently, the X-ray CT apparatus performs the electrocardiographic-synchronous image reconstruction by using the scanning data and the electrocardiographic information obtained in S4 (S5).

Figure 6:
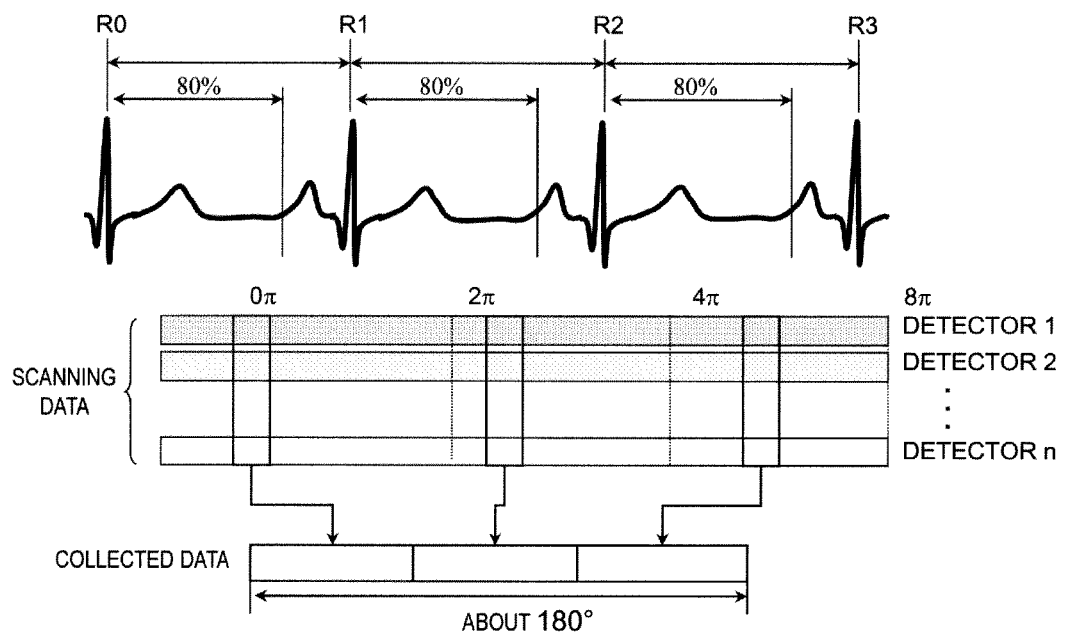
FIG. 6 is a diagram showing an example of an electrocardiographic-synchronous image reconstructing method.

FIG. 6 is a diagram showing an example of the electrocardiographic-synchronous image reconstructing method. In the example of FIG. 6, a tomogram of a relative position 80% of neighboring R-waves is created. Specifically, the image processing device 7 collects divisional scanning data different in scanning angle at the same time phase from scanning data picked up in three heartbeats by only the amount corresponding to the scanning angle (about 180°) necessary for reconstruction. In the example of FIG. 6, divisional scanning data of scanning angles ranging from $0\pi$ to $\pi/3$ are collected from scanning data between R0 and R1, divisional scanning data of scanning angles ranging from $\pi/3$ to $2\pi/3$ (at the position of the X-ray tube 1, $7\pi/3$ to $8\pi/3$) are collected from scanning data between R1 and R2, and divisional scanning data of scanning angles ranging from $2\pi/3$ to it (at the position of the X-ray tube 1, $14\pi/3$ to 5 m) are collected from scanning data between R2 and R3. The image processing device 7 performs image reconstruction on the scanning data of the necessary scanning angles obtained by combining the collected divisional scanning data. In order to create a tomogram at any slice position, interpolation processing is executed between the scanning data obtained from the columns of the X-ray detector 4, whereby a data set at the same slice position is created and the image reconstruction is performed.

Subsequently, the X-ray CT apparatus displays the electrocardiographic-synchronous image reconstructed in S5 on the display device 5 (S6). Then, the operator refers to the electrocardiographic-synchronous image displayed on the display device 5 to make a diagnosis.

As described above, the X-ray CT apparatus according to this embodiment of the present invention is provided with the scanning condition calculating means 12*a* for calculating the period of the periodic motion from the data of the periodic motion, and calculating the scanning condition by using as an index the time resolution rate corresponding to the ratio between the period and the time resolution of the reconstructed image which is generated by the image processing device 7. The X-ray CT apparatus is further provided with means for inputting the time resolution rate by the operator as shown in FIG. 5.

(3. Input as Scanning Mode of Time Resolution Rate)

In the processing of the X-ray CT apparatus described above, the scanning condition corresponding to the time resolution rate input by the operator is calculated. However, in the actual scanning operation, a selectable scanning condition is limited, and it is difficult to propose a scanning condition for implementing a strictly expected time resolution rate to the operator. Therefore, with respect to the input of the time resolution rate shown in FIG. 2 (S2), the time resolution rate may be divided into some ranges, and the operator may adopt a method of selecting a divided range as a scanning mode.

FIG. 7 is a diagram showing an example of a cardiac scanning condition setting screen 21*a* on which the time resolution rate is input as the scanning mode. The same screen items as the cardiac scanning condition setting screen 21 shown in FIG. 5 are represented by the same reference numerals, and the description thereof is omitted. As shown in FIG. 7, the cardiac scanning condition setting screen 21*a* has screen items such as the electrocardiogram display portion 22, the scan type display portion 23, the scan time display portion 24, the bed moving speed display portion 25, a scanning mode input portion 27, etc. In the example of FIG. 7, the scanning mode input portion 27 has three choices of a high image quality mode (=the time resolution rate ranges from 10 to 15%), a standard mode (=the time resolution rate ranges from 15 to 20%) and a high speed mode (=the time resolution rate ranges from 20 to 25%). That is, the time resolution rate is divided into the range from 10% to 15%, the range from 15% to 20% and the range from 20% to 25%, and the operator selects the divided range as a scanning mode. The scanning condition calculating means 12*a* of the computer 12 calculates the scanning condition so that the time resolution rate of the scanning data falls in the range of the time resolution rate of the selected scanning mode. As described above, the X-ray CT apparatus according to the embodiment of the present invention divides the range of the time resolution rate into plural ranges, and displays the scanning mode of each divided range of the time resolution rate on the display device 5, and the scanning condition calculating means 12*a* of the computer 12 may calculate the scanning condition on the basis of the data of the periodic motion so that the time resolution rate of the scanning data falls within the range of the time resolution rate corresponding to the scanning mode selected by the operator.

(4. Display Under Breadth-Holding Training of Time Resolution Rate)

Variation of the cardiac rate under scanning occurs due to various factors such as breath-holding, administration of contrast agent or the like, and it affects the calculation of the scanning condition based on the time resolution rate. In order to suppress this effect, it may be considered to execute a breadth-holding training imitating actual scanning before scanning and grasping a tendency of variation of the cardiac rate in advance. In this case, the scanning condition is calculated by using the average cardiac rate during breadth-holding training as a parameter. However, when the cardiac rate varies rapidly or when the scanning time is long, there is possibility that no optimum scanning condition can be calculated by using even the average cardiac rate. For example, when the scanning time is long, it is necessary to set the scanning condition so that highest time resolution is obtained at a body site which has high importance for diagnosis. Furthermore, in a case where accidental cardiac motion such as premature contraction or the like occurs, a correct scanning condition cannot be necessarily obtained even when the average cardiac rate is calculated. In such a case, the operator may manually determine the scanning condition. Therefore, in order to enable the operator to determine the scanning condition efficiently, a variation graph of the time resolution rate during breadth-holding training may be supplied.

FIG. 8 is a diagram showing an example of a cardiac scanning condition setting screen 21*b* for representing the variation graph of the time resolution rate during a fixed period. The same screen items as the cardiac scanning condition setting screen 21 shown in FIG. 5 are represented by the same reference numerals, and the description thereof is omitted. As shown in FIG. 8, the cardiac scanning condition setting screen 21*b* has screen items such as a variation graph display portion 28 for the time resolution rate, a scan time input portion 24*b*, a bed moving speed input portion 25*b*, etc. The cardiac rate during breadth-holding training and the time variation of the time resolution rate are displayed as graphs on the variation graph display portion 28 for the time resolution rate. The scan time input portion 24*b* and the bed moving speed input portion 25*b* are inputting boxes. The scan time input portion 24*b* and the bed moving speed input portion 25*b* may be text boxes or designed as a selection type such as a pull-down menu or the like.

When the operator inputs a desired scanning condition to the scan time input portion 24*b* and the bed moving speed input portion 25*b* through the input device 13, the computer 12 calculates the time resolution rate when scanning is performed under an input scanning condition, and the calculated time resolution rate is displayed on the display device 5. That is, the time variation of the time resolution rate (based on the time variation of the cardiac rate) when scanning is performed under the input scanning condition is displayed as a graph on the variation graph display portion 28 of the time resolution rate. Accordingly, the variation of the time resolution rate expected when the scanning is performed under the desired scanning condition can be visually checked, and the operator can determine the scanning condition efficiently. The X-ray CT apparatus according to this embodiment of the present invention may calculate the variation of the time resolution rate on the basis of the data of the periodic motion during the fixed period which is measured by the periodic motion measuring device 6, and display the variation of the calculated time resolution rate on the display device 5.

(5. Input of Time Resolution Rate and Cardiac Time Phase Position)

Figure 9:
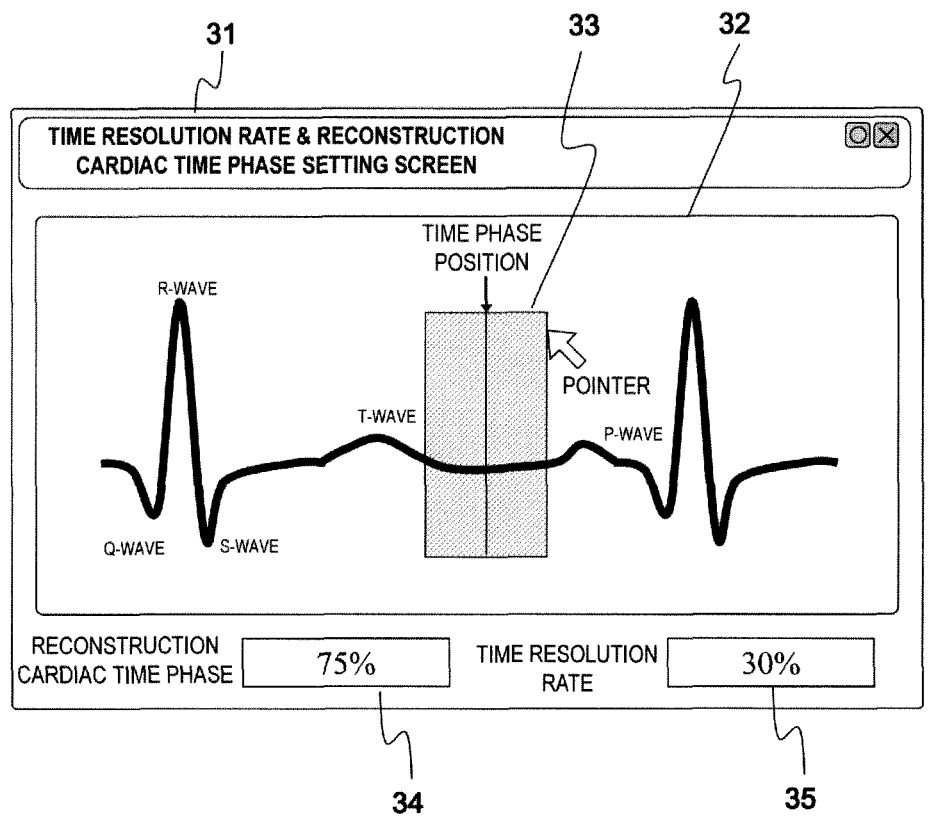
FIG. 9 is a diagram showing an example of a time resolution rate & reconstructed cardiac time phase setting screen 31.

FIG. 9 is a diagram showing an example of a time resolution rate & reconstruction cardiac time phase setting screen 31. By using a screen shown in FIG. 9, the operator may set the time resolution rate and the position of the reconstruction cardiac time phase. As shown in FIG. 9, the time resolution rate & reconstruction cardiac time phase setting screen 31 has screen items such as a heartbeat display portion 32, a reconstruction cardiac time phase display portion 34, a time resolution rate display portion 35, etc. A rectangle 33 is displayed on the heartbeat display portion 32 while superimposed on the waveform of any one heartbeat. The width of the rectangle 33 represents the time resolution rate, and the width of the rectangle 33 is changed by using the input device 13 such as a mouse or the like to adjust the time resolution rate. The center position of the rectangle 33 represents the reconstruction cardiac time phase as a cardiac time phase to be reconstructed, and the reconstruction cardiac time phase is adjusted by moving the position of the rectangle 33. A value which is re-calculated in accordance with the variation of the rectangle 33 is displayed in the reconstruction cardiac time phase display portion 34 and the time resolution rate display portion 35.

The operator can move the rectangle 33, for example, by positioning a displayed pointer in the neighborhood of the center line of the rectangle 33 and executing drag & drop. Furthermore, the operator can expand or narrow the rectangle 33 from the center line in the right and left directions by the same width by positioning the displayed pointer in the neighborhood of any one of the right and left ends of the rectangle 33 and executing drag & drop, for example. The computer 12 inputs the specified lateral width of the rectangle 33 and the position of the center line. Furthermore, the computer 12 calculates values to be displayed in the reconstruction cardiac time phase display portion 34 and the time resolution rate display portion 35 from the input lateral width of the rectangle 33 and the position of the center line thereof.

As described above, the rectangle 33 is displayed while superimposed on the electrocardiographic waveform, and the reconstruction cardiac time phase and the time resolution rate are input on the basis of the lateral width and position of the rectangle 33, whereby the scanning condition can be determined in consideration of the biomedical information of the examinee. For example, it is known that the contraction motion of the heart starts from P-wave as a start point, and it is possible to remove the influence of the contraction motion of the heart on the reconstructed image by setting the time resolution rate and the reconstruction cardiac time phase so that the right side of the rectangle is not overlapped with P-wave. By adjusting the position and width of the rectangle on the electrocardiographic wave as described above, a tomogram having little motional artifact can be obtained with high precision and without being dependent on individual difference of the examinee. As described above, the X-ray CT apparatus according to this embodiment of the present invention may display the rectangle for specifying and inputting the time resolution rate on the display device 5 while the rectangle is superimposed on the waveform representing the data of the periodic motion measured by the periodic motion measuring device 6.

The values to be displayed in the reconstruction cardiac time phase display portion 34 and the time resolution rate display portion 35 are calculated from the lateral width and position of the rectangle 33. However, the input and the output may be interchanged to each other. That is, numerical values may be input into the reconstruction cardiac time phase display portion 34 and the time resolution rate display portion 35 to calculate the lateral width and position of the rectangle 33, and the rectangle 33 may be displayed on the heartbeat display portion 32 on the basis of the calculated value.

(6. Input of Time Resolution Rate Using Part of Waveform)

In the foregoing description, the scanning condition is set so as to obtain the time resolution rate specified by the operator during one heartbeat period. However, the scanning condition may be selected on the basis of the time between feature points of the electrocardiogram. For example, the time from T-wave till R-wave may be set as the time between the feature points of the electrocardiogram. In this case, the operator specifies the time from T-wave till R-wave and a desired time resolution rate, and the computer 12 sets a scanning condition on the basis of the time from T-wave till R-wave. When the cardiac rate varies, it is generally known that the cardiac rate does not greatly vary for the time from R-wave till T-wave, but it varies for the time from T-wave till R-wave. That is, on the basis of the time from T-wave till R-wave, the scanning condition can be set interlockingly with the cardiac rate, and thus the scanning condition can be set with higher precision. As described above, the scanning condition calculating means 12a provided to the computer 12 may calculate the scanning condition on the basis of the time from T-wave till R-wave during one period.

(7. Display of Sample Image with Time Resolution Rate Set as Index)

FIG. 10 is a diagram showing an example of a cardiac scanning condition setting screen 21c. The same screen items as the cardiac scanning condition setting screen 21 shown in FIG. 5 are represented by the same reference numerals, and the description thereof is omitted. As shown in FIG. 10, the cardiac scanning condition setting screen 21c has screen items such as the electrocardiogram display portion 22, the scan type display portion 23, the scan time display portion 24, the bed moving speed display portion 25, the time resolution rate input portion 26, a sample image display portion 29, etc.

A sample image corresponding to a time resolution rate specified by the operator may be displayed on the cardiac scanning condition setting screen 21c so that the operator can easily determine the time resolution rate. According to the conventional method of selecting the scanning condition on the basis of the time resolution, the image quality varies in accordance with the cardiac rate of the examinee in spite of the same time resolution, and thus it is necessary to provide sample images whose number corresponds to the number of combinations of the time resolution and the cardiac rate. This is not realistic. However, according to the method of determining the scanning condition on the basis of the time resolution rate according to this embodiment of the present invention, only sample images based on the time resolution rate may be provided. For example, when the time resolution rate is input at an interval of 5%, twenty sample images may be provided, and this is easily implemented.

In the example of FIG. 10, the sample image displayed on the sample image display portion 29 is updated every time the operator changes the numerical value on the time resolution rate input portion 26. As described above, the X-ray CT apparatus according to this embodiment of the present invention displays the sample image corresponding to the time resolution rate on the display device 5. Accordingly, the operator can adjust the time resolution rate while checking the image quality of the sample image.

The preferred embodiments of the X-ray CT apparatus, etc. according to the present invention are described above with reference to the accompanying drawings. However, the present invention is not limited to these examples. It is clear that persons skilled in the art can make various modifications and alterations within the scope of the technical idea disclosed in this application, and it is understood that they belong to the technical scope of the present invention.

DESCRIPTION OF REFERENCE NUMERALS

1 X-ray tube, 2 scanner gantry, 3 bed, 4 X-ray detector, 5 display device, 6 periodic motion measuring device, 7 image processing device, 8 rotational disc, 9 collimator, 10 rotational driving device, 11 measurement control device, 12 computer, 12a scanning condition calculating means, 13 input device

The invention claimed is:

1. An X-ray CT apparatus comprising:
   an X-ray source for applying X-ray;
   an X-ray detector that is disposed so as to face the X-ray source while an examinee is sandwiched between the X-ray source and the X-ray detector and detects an X-ray dose transmitted through the examinee;
   a gantry that has the X-ray source and the X-ray detector mounted therein and is rotatable around the examinee;
   a bed that is movable while the examinee is put on the bed;
   a control device that controls the X-ray source, the X-ray detector, the gantry and the bed;
   a periodic motion measuring device that measures a periodic motion of the examinee;
   an image processing device that generates a reconstructed image of the examinee at any phase of the periodic motion on a basis of data of the X-ray dose and data of the periodic motion; and
   a display device that displays the reconstructed image, characterized by comprising
   scanning condition calculating means that calculates a period of the periodic motion from the data of the periodic motion and calculates a scanning condition by using as an index a time resolution rate corresponding to a ratio between a time resolution of the reconstructed image and the period of the periodic motion of the examinee.

2. The X-ray CT apparatus according to claim 1, further comprising means through which an operator inputs the time resolution rate, wherein the scanning condition calculating means calculates the scanning condition on a basis of the data of the periodic motion so as to satisfy the time resolution rate input by the operator.

3. The X-ray CT apparatus according to claim 1, further comprising a user interface that displays, for user selection, plural ranges of time resolution rates and corresponding scanning modes on the display device, wherein the scanning condition calculating means calculates the scanning condition on a basis of the data of the periodic motion so as to fall into the range of the time resolution rate corresponding to the scanning mode selected by the operator.

4. The X-ray CT apparatus according to claim 1, further comprising means that calculates variation of the time resolution rate on a basis of the data of the periodic motion of a fixed period measured by the periodic motion measuring device and displays the calculated variation of the time resolution rate on the display device.

5. The X-ray CT apparatus according to claim 1, further comprising means that displays a rectangle for specifying and inputting the time resolution rate on the display device while superimposing the rectangle on a waveform representing the data of the periodic motion measured by the periodic motion measuring device.

6. The X-ray CT apparatus according to claim 1, wherein the periodic motion is cardiac pulsation of the examinee, and the scanning condition calculating means calculates a scanning condition with respect to a time from T-wave till R-wave in one period.

7. The X-ray CT apparatus according to claim 1, further comprising means that displays a sample image corresponding to the time resolution rate on the display device.

8. The X-ray CT apparatus according to claim 1, wherein the control device controls at least one of the X-ray source, the X-ray detector, the gantry and the bed based on the scanning condition determined by using the time resolution rate.

* * * * *